US012558305B2

(12) United States Patent
    Engler et al.

(10) Patent No.: US 12,558,305 B2
(45) Date of Patent: Feb. 24, 2026

(54) ORAL ARTICLES AND METHODS OF USE

(71) Applicant: Solventum Intellectual Properties Company, Maplewood, MN (US)

(72) Inventors: Amanda C. Engler, Woodbury, MN (US); Katie F. Wlaschin, St. Paul, MN (US); Hannah C. Cohen, St. Paul, MN (US); Yizhong Wang, Woodbury, MN (US); Tiffany T. Ton, Woodbury, MN (US); Jie Yang, Woodbury, MN (US); Joel D. Oxman, Minneapolis, MN (US); Emily M. Wollmuth, Ithaca, NY (US)

(73) Assignee: Solventum Intellectual Properties Company, Maplewood, MN (US)

( * ) Notice: Subject to any disclaimer, the term of this patent is extended or adjusted under 35 U.S.C. 154(b) by 865 days.

(21) Appl. No.: 17/419,397

(22) PCT Filed: Dec. 26, 2019

(86) PCT No.: PCT/IB2019/061380
§ 371 (c)(1),
(2) Date: Jun. 29, 2021

(87) PCT Pub. No.: WO2020/136606
PCT Pub. Date: Jul. 2, 2020

(65) Prior Publication Data
US 2022/0062157 A1     Mar. 3, 2022

Related U.S. Application Data

(60) Provisional application No. 62/786,358, filed on Dec. 29, 2018.

(51) Int. Cl.
| | | |
|---|---|---|
| *A61K 8/92* | (2006.01) | |
| *A61K 8/02* | (2006.01) | |
| *A61Q 11/00* | (2006.01) | |

(52) U.S. Cl.
CPC ............ *A61K 8/922* (2013.01); *A61K 8/0233* (2013.01); *A61Q 11/00* (2013.01); *A61K 2800/92* (2013.01); *A61K 2800/95* (2013.01)

(58) Field of Classification Search
CPC .. A61K 8/922; A61K 8/0233; A61K 2800/92; A61K 2800/95; A61K 8/0216; A61K 8/345; A61K 8/361; A61K 8/73; A61K 8/731; A61K 8/737; A61K 9/006; A61K 47/10; A61K 47/26; A61K 47/34; A61K 47/36; A61K 47/38; A61K 47/46; A61Q 11/00; A61P 1/02
See application file for complete search history.

(56) References Cited

U.S. PATENT DOCUMENTS

| | | | |
|---|---|---|---|
| 4,906,455 | A | 3/1990 | Hoerman |
| 4,971,788 | A | 11/1990 | Tabibi |
| 5,130,122 | A | 7/1992 | Tabibi |
| 5,332,595 | A | 7/1994 | Gaonkar |
| 5,401,496 | A | 3/1995 | Fitzig |
| 5,482,722 | A | 1/1996 | Cook |
| 5,496,558 | A | 3/1996 | Napolitano |
| 5,523,098 | A | 6/1996 | Synosky |
| 5,614,207 | A | 3/1997 | Shah |
| 5,618,522 | A | 4/1997 | Kaleta |
| 5,711,936 | A | 1/1998 | Hill |
| 5,733,529 | A | 3/1998 | Hill |
| 6,060,078 | A | 5/2000 | Lee |
| 6,159,459 | A | 12/2000 | Hunter |
| 6,183,775 | B1 | 2/2001 | Ventouras |
| 6,596,298 | B2 | 7/2003 | Leung |
| 6,682,756 | B1 | 1/2004 | Horstmann |
| 7,025,983 | B2 | 4/2006 | Leung |
| 7,407,669 | B2 | 8/2008 | Leung |
| 7,648,712 | B2 | 1/2010 | Bess |
| 7,867,509 | B2 | 1/2011 | Leung |
| 8,197,851 | B2 | 6/2012 | Bos |

(Continued)

FOREIGN PATENT DOCUMENTS

| | | |
|---|---|---|
| AU | 2012205140 | 8/2012 |
| CN | 106666055 | 5/2017 |

(Continued)

OTHER PUBLICATIONS

Arya, "Fast Dissolving Oral Films: An Innovative Drug Delivery System and Dosage Form", International Journal of ChemTech Research, Jan.-Mar. 2010, vol. 2, No. 1, pp. 576-583.
Dixit, "Oral strip technology: Overview and future potential", Journal of Controlled Release, 2009, vol. 139, No. 2, pp. 94-107.
Donaldson, "Xerostomia Treatment: A Systematic Approach to Xerostomia diagnosis and Management", Compendium eBook Continuing Education, Nov.-Dec. 2018, vol. 39, No. 20, 12 pages.
Donaldson, "Xerostomia Update: Comprehensive and Systematic Diagnosis and Management", Jan. 2020, CDE World eBook, Continuing Dental Education, Dental Learning Systems, LLC, vol. 7, No. 158, 16 pages.

(Continued)

*Primary Examiner* — Lezah Roberts
*Assistant Examiner* — Abdulrahman Abbas

(57) ABSTRACT

Articles that include from 20 wt-% to 45 wt-% of one or more plant based oils based on the total weight of the article; from 50 wt-% to 70 wt-% of one or more polymer film formers based on the total weight of the article; and from 5 wt-% to 15 wt-% of one or more humectants based on the total weight of the article. Further articles comprises this combination of oil, film former and humectant as a first layer adjacent to which a second layer comprises a mucoadhesive polymer. The articles may be used to prevent formation or maintenance of biofilm in an oral tissue, affect hydration loss in an oral tissue, affect lubricity or lubriciousness in an oral tissue or treat xerostomia or dry mouth. Preferred polymer film formers include pullulan, xanthan gum, HP guar, ethyl cellulose and carrageenan.

20 Claims, 1 Drawing Sheet

(56)                References Cited

U.S. PATENT DOCUMENTS

| 8,367,650 | B2 | 2/2013 | Desjonqueres |
| 8,460,689 | B2 | 6/2013 | Wlaschin |
| 8,540,970 | B2 | 9/2013 | Rodriguez-Vilaboa |
| 8,647,608 | B2 | 2/2014 | Yang |
| 8,758,803 | B2 | 6/2014 | Müller |
| 8,968,709 | B2 | 3/2015 | Yang |
| 9,289,369 | B2 | 3/2016 | Boyd |
| 9,320,690 | B2 | 4/2016 | Ontumi |
| 9,539,205 | B2 | 1/2017 | Haug |
| 9,724,278 | B2 | 8/2017 | Lambert |
| 9,730,865 | B2 | 8/2017 | Sullivan |
| 9,968,547 | B2 | 5/2018 | Okay |
| 10,413,503 | B2 | 9/2019 | Okay |
| 10,744,082 | B2 | 8/2020 | Okay |
| 2003/0118628 | A1 | 6/2003 | Tutuncu |
| 2004/0141927 | A1 | 7/2004 | Johnson |
| 2004/0156794 | A1 | 8/2004 | Barkalow |
| 2005/0152972 | A1 | 7/2005 | Singh |
| 2005/0281772 | A1 | 12/2005 | Bromley |
| 2006/0204559 | A1 | 9/2006 | Bess |
| 2006/0263412 | A1 | 11/2006 | Pan |
| 2007/0031561 | A1 | 2/2007 | Lakkis |
| 2007/0154411 | A1 | 7/2007 | Barth |
| 2007/0183985 | A1 | 8/2007 | Tallia |
| 2007/0190090 | A1 | 8/2007 | Brown |
| 2008/0020024 | A1 | 1/2008 | Kulkarni |
| 2008/0241080 | A1 | 10/2008 | Rodriguez-Vilaboa |
| 2009/0081291 | A1 | 3/2009 | Gin |
| 2009/0081294 | A1* | 3/2009 | Gin ........................... A61P 1/00 |
| | | | 424/747 |
| 2009/0136893 | A1* | 5/2009 | Zegarelli .............. A61C 19/066 |
| | | | 433/80 |
| 2009/0311200 | A1 | 12/2009 | Lambert |
| 2010/0098791 | A1 | 4/2010 | Rodriguez-Vilaboa |
| 2010/0233221 | A1 | 9/2010 | Folmer |
| 2010/0247644 | A1 | 9/2010 | Domb |
| 2011/0027328 | A1 | 2/2011 | Baig |
| 2011/0104081 | A1 | 5/2011 | Scott |
| 2011/0171342 | A1 | 7/2011 | Phillips, III |
| 2012/0058158 | A1 | 3/2012 | Booles |
| 2012/0238635 | A1* | 9/2012 | Puigvert Colomer ...................... |
| | | | A61K 31/155 |
| | | | 514/635 |
| 2013/0052146 | A1 | 2/2013 | Yang |
| 2013/0269133 | A1 | 10/2013 | Ontumi |
| 2013/0309291 | A1 | 11/2013 | Stoll |
| 2014/0120150 | A1* | 5/2014 | McDonald, III ....... A61K 9/006 |
| | | | 424/78.3 |
| 2014/0155457 | A1 | 6/2014 | Nho |
| 2015/0216887 | A1 | 8/2015 | Derrieu |
| 2015/0290107 | A1 | 10/2015 | Okay |
| 2016/0339026 | A1* | 11/2016 | Noncovich .......... A61K 8/4913 |
| 2019/0083220 | A1 | 3/2019 | Wlaschin |
| 2021/0161800 | A1 | 6/2021 | Okay |

FOREIGN PATENT DOCUMENTS

| EP | 1674078 | 6/2006 |
| EP | 1676557 | 7/2006 |
| EP | 2027852 | 2/2009 |
| GB | 2139919 | 11/1984 |
| GB | 2242358 | 4/1994 |
| WO | WO 1996-039116 | 12/1996 |
| WO | WO 1999-029686 | 6/1999 |
| WO | WO 2002-022096 | 3/2002 |
| WO | WO 2004-096192 | 11/2004 |
| WO | WO 2009-014907 | 1/2009 |
| WO | WO 2009-042968 | 4/2009 |
| WO | WO 2012-087279 | 6/2012 |
| WO | WO 2012-087280 | 6/2012 |
| WO | WO 2012-087281 | 6/2012 |
| WO | WO 2014-053263 | 4/2014 |
| WO | WO 2014-098868 | 6/2014 |
| WO | WO 2014-166994 | 10/2014 |
| WO | WO 2016-207299 | 12/2016 |
| WO | WO 2017-042275 | 3/2017 |
| WO | WO 2017-205230 | 11/2017 |
| WO | WO 2017-218421 | 12/2017 |
| WO | WO 2018-029671 | 2/2018 |
| WO | WO 2019-123171 | 6/2019 |
| WO | WO 2019-123261 | 6/2019 |
| WO | WO 2020-136604 | 7/2020 |
| WO | WO 2020-136620 | 7/2020 |

OTHER PUBLICATIONS

"Dry Mouth—Seniors Oral Health", Washington Dental Service Foundation [on line], 2017, [retrieved from the internet on Apr. 6, 2022], URL <http://seniorsoralhealth.org/dry-mouth/?doing_wp_cron=1471029828.7616550922393798828125>, 2 pages.

"Frozen Reverse Spherification—Molecular Recipes", KQ2 Ventures LLC [on line], Mar. 2014, [retrieved from the internet on Apr. 4, 2022], URL <http://www.molecularrecipes.com/spherification-class/frozen-reverse-spherification/>, 5 pages.

Furness, "Interventions for the Management of Dry Mouth: Topical Therapies (Review)", Cochrane database of systematic reviews, 2011, vol. 12, No. 12, pp. 1-93.

Horne, "What Causes Dry Mouth", MedicineNet [on line], Mar. 2020, [retrieved from the internet on Apr. 4, 2022], URL <https://www.medicinenet.com/dry_mouth/article.htm>, 8 pages.

Kelly, "Bioadhesive, rheological, lubricant and other aspects of an oral gel formulation intended for the treatment of xerostomia", International Journal of Pharmaceutics, 2004, vol. 278, pp. 391-406.

Patel, "Effect of subgingival application of topical ozonated olive oil in the treatment of chronic periodontitis: a randomized, controlled, double blind, clinical and microbiological study". Minerva Stomatol, 2012. vol. 61 No. 9 pp. 381-398.

Patel, "Therapeutic effect of topical ozonated oil on the epithelial healing of palatal wound sites: a planimetrical and cytological study". Journal of Investigative and Clinical Detistry, Jul. 2011, vol. 2, No. 4, pp. 248-258.

"Reverse Spherification—Molecular Recipes", KQ2 Ventures LLC [on line], Mar. 2014, [retrieved from the internet on Apr. 4, 2022], URL <http://www.molecularrecipes.com/spherification-class/reverse-spherification/>, 10 pages.

Russo, "A focus on mucoadhesive polymers and their application in buccal dosage forms", Journal of Drug Delivery Science and Technology, 2016, vol. 32, pp. 113-125.

Saha, "Hydrocolloids as thickening and gelling agents in food: a critical review", Journal of Food Science and Technology, Nov.-Dec. 2010, vol. 47 No. 6 pp. 587-597.

Video: "Encapsulation of Oil Isomalt Technical Sugar" Oct. 2013 URL <https://www.youtube.com/watch?v=4t8BzzaX-iY6>, 00:01:24 HRS.

Zhang, "Food-grade filled hydrogels for oral delivery of lipophilic active ingredients: Temperature-triggered release microgels", Food Research International, 2015, vol. 69, pp. 274-280.

International Search Report for PCT International Application No. PCT-IB2019-061378, mailed on Jun. 23, 2020, 6 pages.

International Search Report for PCT International Application No. PCT-IB2019-061380, mailed on Apr. 29, 2020, 6 pages.

International Search Report for PCT International Application No. PCT-IB2019-061406, mailed on Apr. 14, 2020, 4 pages.

* cited by examiner

ORAL ARTICLES AND METHODS OF USE

CROSS REFERENCE TO RELATED APPLICATIONS

This application is a national stage filing under 35 U.S.C. 371 of PCT/IB2019/061380, filed 26 Dec. 2019, which claims the benefit of U.S. Provisional Application No. 62/786,358, filed 29 Dec. 2018, the disclosures of each of which are incorporated by reference herein in their entireties.

SUMMARY

Disclosed herein are articles including from 20 wt-% to 45 wt-% of one or more plant based oils based on the total weight of the article; from 50 wt-% to 70 wt-% of one or more polymer film formers based on the total weight of the article; and from 5 wt-% to 15 wt-% of one or more humectants based on the total weight of the article.

Methods of preventing, inhibiting, disrupting, or any combination thereof the formation or maintenance of a biofilm in an oral tissue, the methods including contacting an oral tissue with disclosed articles.

Methods of affecting hydration loss in an oral tissue, the methods including contacting an oral tissue with disclosed articles.

Methods of affecting lubricity or lubriciousness in an oral tissue, the methods including contacting an oral tissue with disclosed articles.

Methods of affecting the effects of xerostomia, dry mouth, or both, the methods including contacting an oral tissue with disclosed articles.

Articles including a first layer including from 20 wt-% to 45 wt-% of one or more plant based oils based on the total weight of the article; from 50 wt-% to 70 wt-% of one or more polymer film formers based on the total weight of the article; and from 5 wt-% to 15 wt-% of one or more humectants based on the total weight of the article; and a second layer adjacent to the first layer, the second layer including a mucoadhesive polymer.

The above summary is not intended to describe each embodiment of the present disclosure. The details of one or more embodiments of the present disclosure are also set forth in the description below. Other features, objects, and advantages of the present disclosure will be apparent from the description and from the claims.

BRIEF DESCRIPTION OF DRAWINGS

The disclosure may be more completely understood in consideration of the following detailed description of various illustrative embodiments in connection with the accompanying drawings, in which.

DETAILED DESCRIPTION

Figure 1A:
FIG. 1A shows an illustrative article having a single layer.

Xerostomia or dry mouth is a common condition that results from insufficient saliva volume. It is increasingly prevalent in the aging population and is a side-effect of many medications, as well as cancer treatment. Severe cases of xerostomia are often related to salivary gland dysfunction, known as Sjögren's Syndrome.

The lack of moisture and lubrication typically provided by saliva has a range of negative effects on oral tissue (soft tissue) ranging from mild discomfort to extremely painful and infected mouth sores. The persistent discomfort and dryness can also contribute to larger health issues by causing disruption of sleep, and impairing one's ability to talk (socialize, may impact psychological health) and eat (may impact nutrition). Dry buccal tissue is a less effective barrier and more susceptible to penetration by physical irritants such as toxins and carcinogens in foods, beverages and tobacco.

Saliva is also the mouth's primary defense against tooth decay. Healthy saliva flow helps prevent cavities by physically removing bacteria from the oral cavity before they can become attached to tooth and tissue surfaces and form a protected biofilm. The flow of saliva also helps dilute sugars and acids introduced by intake of food and beverages. The buffering capacity neutralizes acids and aids in the digestive process. The presence of calcium and phosphate salts provides continuous opportunity for re-mineralization of tooth enamel, serving to reverse the tooth decay process.

Many who suffer with xerostomia use separate products to address hard tissue health and soft tissue comfort. For soft tissue comfort, saliva substitute products are typically designed to provide lubrication and moisture. The format of these products is varied, and includes viscous gels/pastes, sprays, rinses, mints, and slow-release tablets. These are applied multiple-times per day or as needed for comfort. For hard-tissue health, different treatments are used to directly address cavity prevention (antiseptic rinses, fluoride products, calcium/phosphate treatments). Often "dry mouth-friendly" versions of products, such as toothpastes and mouth rinses are recommended. Dry mouth friendly products typically have a neutral pH and do not contain alcohol or other irritating components (e.g. anionic surfactants or emulsifiers).

There is a desire to design a single product that effectively and easily addresses the need for dry mouth symptom relief (soft tissue comfort) and oral health preventative benefits (tooth enamel and cavity protection). A fully ingestible, strip or tape product is well suited for this purpose. It addresses both the health of hard-tissue (water phase) and soft tissue (oil phase).

Disclosed herein are articles that can be utilized as oral articles, for example. Disclosed articles can be in the form of films for example. Illustrative films can be in the shape of tape or strips. Disclosed articles can be formed by disposing a composition that includes one or more solvents as well as components of disclosed articles and then evaporating at least some of the one or more solvents. Disclosed articles therefore generally have higher weight percentages of components than do compositions that can be utilized to form the one or more articles. In some embodiments, compositions for making disclosed articles can include water as a solvent.

Disclosed articles, one or more components in an article, or both can be characterized as edible. Referring to a component, composition or article as edible can mean that the particular ingredient, composition or article is safe for daily, long-term ingestion at recommended use levels. In some embodiments, the GRAS (generally regarded as safe) list from the United States Food and Drug Administration (FDA) can be utilized to determine if a component is edible at the levels utilized in a composition.

Disclosed articles include one or more useful oil, one or more polymer film formers and one or more humectants.

Disclosed articles include one or more oils. Useful oils can include any oils but, in some embodiments, can include plant-based oils. For example, plant-based oils can be extracted from various plants (e.g., soybean, canola, and chili), seeds (e.g., sesame and sunflower), nuts (e.g., walnut and macadamia), and fruits (e.g., palm, olive, and coconut), for example. In some embodiments, useful oils can include one or more than one that are liquids at room temperature (25° C.). The articles can include a single edible oil, or as many as two, three, four, five or more edible oils. Examples of suitable edible oils can include, but are not limited to, sunflower oil (including high oleic sunflower oil), safflower oil (including high oleic safflower oil), olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, watermelon seed oil, lemon oil, orange oil, thistle oil, tomato seed oil, almond oil, *perilla* oil, canola oil, pistachio oil, hazelnut oil, avocado oil, and the like, and mixtures or fractions thereof.

Disclosed articles can include not less 15 percent of one or more oils based on the total weight of the article, not less than 20 percent of one or more oils based on the total weight of the article, not less than 23 percent of one or more oils based on the total weight of the article, not less than 25 percent of one or more oils based on the total weight of the article, or not less than 30 percent of one or more oils based on the total weight of the article. Disclosed articles can include not greater than 45 percent of one or more oils based on the total weight of the article, not greater than 40 percent of one or more oils based on the total weight of the article, not greater than 35 percent of one or more oils based on the total weight of the article, not greater than 30 percent of one or more oils based on the total weight of the article, or not greater than 28 percent of one or more oils based on the total weight of the article.

Disclosed articles also include one or more polymer film formers. Illustrative useful polymer film formers can include, for example pullulan, hydroxypropylmethyl cellulose, hydroxyethyl cellulose, hydroxypropyl cellulose, ethyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein, xanthan gum, locust bean gum, carrageenan, and combinations thereof. In some embodiments, disclosed articles can include pullulan, xanthan gum, carrageenan, or combinations thereof as polymer film formers. In some embodiments, disclosed articles can include not less than 50 percent of one or more polymer film formers based on the total weight of the article, not less than 52 percent of one or more polymer film formers based on the total weight of the article, or not less than 55 percent of one or more polymer film formers based on the total weight of the article. In some embodiments, disclosed article can include not greater than 70 percent of one or more polymer film formers based on the total weight of the article, not greater than 67 percent of one or more polymer film formers based on the total weight of the article, or not greater than 65 percent of one or more polymer film formers based on the total weight of the article.

Disclosed articles also include one or more humectants. Illustrative useful humectants can include, for example glycerol, sorbitol, xylitol, maltitol, propylene glycol, hexylene glycol, butylene glycol, erythritol, isomalt or combinations thereof. In some embodiments, disclosed articles can include one or more humectants including for example glycerol, xylitol, erythritol, or combinations thereof. Humectants such as xylitol, erythritol, or combinations thereof may be especially useful because they would provide benefits to the hard tissues of the mouth as well as provide humectant properties. In disclosed articles, the one or more humectant can be present in an amount of not less than 5 percent based on the total weight of the article, or not less than 7 percent based on the total weight of the article. In disclosed articles, the one or more humectant can be present in an amount of not greater than 15 percent based on the total weight of the article, or not greater than 12 percent based on the total weight of the article.

Disclosed articles can also optionally include additional components other than those discussed above. Illustrative optional components can include, for example, sweeteners (e.g., non-carcinogenic sweeteners), mineral salts, buffering components, flavorants, preservative agents, or combinations thereof. Other optional beneficial ingredients can also be included at appropriate levels such as, aloe vera (multi-benefit), folic acid (related to B12), hyaluronic acid, ceramides, arginine, betaines or oxygenated glycerol triesters, vitamin E (antioxidant), vitamin B12, EDTA, cetyl pyridinium chloride, chlorhexidine, other antiseptics, etc., or combinations thereof.

In some embodiments, disclosed articles can include flavorants including for example, peppermint, strawberry, butter, vanilla, coconut, almond, bubble gum, berry, fruit punch, butterscotch, caramel, or combinations thereof. In some embodiments, some flavorants, e.g., mint, citrus, etc. can also be advantageous because they stimulate salivary production when utilized in articles. Artificial sweeteners may also be used (*stevia*, aspartame, sucralose, neotame, acesulfame potassium (Ace-K), saccharin, and advantame, for example). In some embodiments, disclosed articles can include one or more sweeteners including for example, non-cariogenic polyols, or sugar substitutes (e.g., sucralose). In some embodiments, disclosed articles can include non-cariogenic polyol sweeteners such as xylitol, sorbitol, maltitol, erythritol, or combinations thereof. In some embodiments, disclosed articles can include non-cariogenic polyol sweeteners such as xylitol, sorbitol, or combinations thereof. In articles that include optional sweeteners, the sweetener can be present in an amount that is not less than 2.5 percent based on the total weight of the article or not less than 1 percent based on the total weight of the article. In some embodiments, an optional sweetener can be present in an amount that is not greater than 20 percent based on the total weight of the article or not greater than 15 percent based on the total weight of the article.

In some embodiments, disclosed articles can optionally include one or more minerals that may be useful or beneficial for ingestion or oral health. Illustrative optional minerals that can be included in disclosed articles can include calcium (Ca), phosphorus (P), magnesium (Mg), fluorine (F), iron (Fe), strontium (Sr), zinc (Zn), potassium (K), or combinations thereof. In some embodiments, some minerals can be provided by including magnesium chloride ($MgCl_2$), calcium chloride ($CaCl_2$)), strontium chloride, zinc chloride, zinc gluconate, potassium nitrate, potassium phosphate dibasic ($KH_2PO_4$), or combinations thereof. In some embodiments, where fluorine is included, it can be included as the fluoride ion (F—) in salt form ($MgF_2$, $CaF_2$, etc.), at a concentration that is not greater than 4 milligrams per liter (mg/L).

In some embodiments, disclosed articles can include one or more preservatives to render the article microbiologically stable, to increase the microbiological stability thereof, or some combination thereof. In some embodiments, useful preservatives include those that work at a neutral pH, do not detrimentally affect taste, are edible, are effective against a broad spectrum of pathogens, or combinations thereof. Specific illustrative useful preservatives can include GEOGARD® preservatives, which are commercially available from Lonza (Basel, Switzerland), and include salicyclic acid, benzyl alcohol, sodium benzoate, potassium sorbate, parabens, natural preservatives, polyglyceryl esters, monolaurin, 1,2 octanediol, caprylic/capric triglycerides, DHA, aloe vera, potassium sorbate, CPC, PHMB, and CHG for example.

In some embodiments, articles that include neither guar nor ethyl cellulose as film formers can include not greater than 36 percent of at least one oil based on the total weight of the article. Such articles can include not less than 55 percent of one or more film formers based on the total weight of the article. In some embodiments, articles that include a mixture of guar and ethyl cellulose as film formers for example can include not greater than 28 percent of at least one oil based on the total weight of the article. Such articles can include not less than 65 percent of one or more film formers based on the total weight of the article. In some embodiments, articles that include guar but not ethyl cellulose as a film former for example can include not greater than 26 percent of at least one oil based on the total weight of the article. Such articles can include not less than 65 percent of one or more film formers based on the total weight of the article.

Disclosed articles can have varied properties. In some embodiments, disclosed articles can be described by the pH thereof, the viscosity thereof, the stability thereof, various other properties, or combinations thereof.

In some embodiments, disclosed articles can have a pH that is acceptable for use in the mouth of a person, for example. In some embodiments, disclosed articles can have a pH from 4.5 to 9.5, for example. In some embodiments, the article can have a pH in a more neutral range from 5.0-8.5 or 5.5-8.5 for example, as dry mouth sufferers can have a higher sensitivity to pH. The article can naturally have such a pH or can be buffered to have a pH in a useful, e.g., a "neutral" range.

In some embodiments, disclosed articles can be described as a stable oil phase encapsulated in a water soluble film former. When the article is placed in the mouth, the article dissolves and may form a protective, lubricating coating in the mouth. The coating can function to provide relatively long term conform for soft tissue and may additionally, optionally protect hard tissue. Disclosed articles can be described by their integrity, oily residue or lack thereof, film stretchiness (e.g., stretch versus brittle feel), feel (e.g., sticky versus not sticky, oily versus not oily). The time it takes for an article to dissolve in the mouth of a user can also be described and/or measured. In some embodiments, the time it takes an article to dissolve can be estimated using a dissolution study, for example.

Disclosed articles can exist in the form of a strip, a roll or tape, or similar forms. In some embodiments, disclosed articles can be associated with a liner that can function to maintain separation between different portions of a roll or tape of articles for example or separate strips.

In some embodiments, disclosed articles can have desired effects when utilized. Such effects can include, for example the article's effect on biofilms, the article's effect on plaque buildup, the article's effect on water loss, the article's ability to maintain or provide lubricating properties, resist dilution or wash-off by saliva or water, or drinking and eating in general or combinations thereof.

In some embodiments, disclosed articles can prevent, inhibit, disrupt the formation or maintenance of a biofilm in an area contacted with the article. The area contacted can be in vivo or in vitro. In some embodiments, an article can prevent, inhibit, disrupt the formation or maintenance of a biofilm in a mouth of a user where the article was applied to the mouth, for example via spraying the article into the mouth when compared to a mouth without the article applied thereto. In some embodiments, an article can prevent, inhibit, disrupt the formation or maintenance of a biofilm in a container in which a biofilm exists and the article was applied to the container via contact when compared to a container without the article contacted thereto. Preventing, inhibiting, disrupting, or some combination thereof the formation or maintenance of biofilms can be measured using a modified version of the MBEC assay (described in ASTM E2799), which measures disruption of strep *mutans* biofilms grown on special pegs in a microtiter plate. The biofilms growing on the pegs are treated by periodic submersion into test materials, followed by washing in saliva and water. The biofilm remaining on each peg following treatment is quantified by measuring the amount of fluorescently labeled bacteria that eluted from the pegs at the end of the treatment cycles (see example). In some embodiments, disclosed articles can affect the buildup of plaque in an area contacted by the article. The area contacted can be in vivo or in vitro. In some embodiments, an article can decrease plaque buildup on at least one tooth in a mouth of a user where the article was applied to the mouth, for example via contacting the article into the mouth when compared to a mouth without the article applied thereto. In some embodiments, an article can decrease plaque buildup in a container in which plaque can develop and the article was applied to the container via pouring, spraying, etc. when compared to a container without the article contacted thereto. Decreasing plaque buildup can be measured by a variety of methods in vivo including for example plaque scoring, dyeing of plaque, etc..

In some embodiments, disclosed articles can affect hydration loss in an area contacted by the articles. The area contacted can be in vivo or in vitro. In some embodiments, an article can decrease hydration loss in a mouth of a user where the article was applied to the mouth, for example via contacting the article into the mouth when compared to a mouth without the article applied thereto. In some embodiments, an article can decrease hydration loss from a tissue in which hydration can be lost and the article was applied to the tissue via contact when compared to a tissue without the article applied thereto. Hydration loss can be measured by exposing treated tissues of uniform size to a controlled 37° C. environment for a set time period (4 hrs), and recording the % weight loss from the treated tissue sample. The treated tissue is then exposed to high temperature to rid the sample of all water (95° C./4 hrs and 115° C./4 hrs). The water lost at 4 hrs is divided by the total water loss (after the 115° C. step) and is indicative of the water lost from the tissue at 4 hrs.

In some embodiments, disclosed articles can affect lubricity or lubriciousness of an area contacted by the article. The area contacted can be in vivo or in vitro. In some embodiments, an article can maintain or increase lubricity in a mouth of a user where the article was applied to the mouth, for example via contacting the article into the mouth when compared to a mouth without the article applied thereto. In some embodiments, an article can provide lubricating properties to a mouth to the same degree that saliva can, for example. In some embodiments, an article can maintain or increase lubricity on a substrate in which lubricity can be lost and the article was applied to the substrate via contact when compared to a substrate without the article applied thereto. Lubricity or the ability to provide lubricating properties can be measured by the friction coefficient relative to a suitable substrate. A low friction coefficient (comparable to saliva) is desired.

Figure 1B:
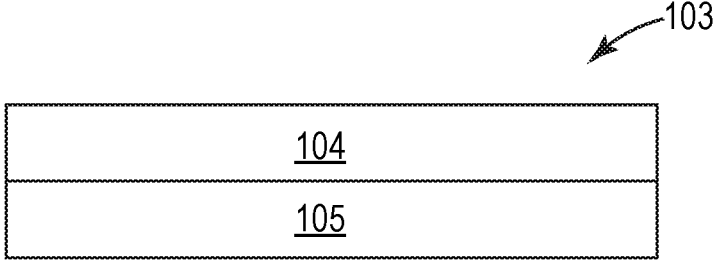
FIG. 1B shows an illustrative article having two layers.
Figure 1C:
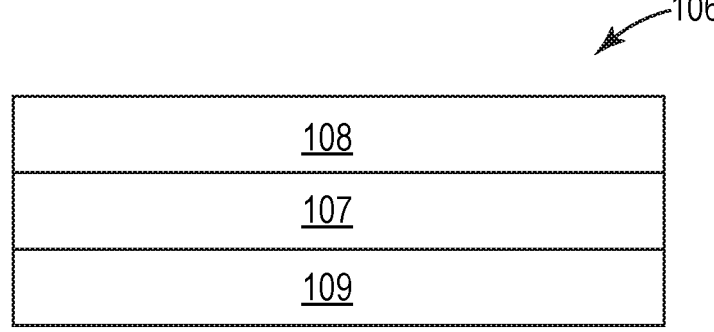
FIG. 1C shows an illustrative article having three layers.

Disclosed articles can also include more than one layer, such as that depicted by the single layer article 100 seen in FIG. 1A. In such articles, the first layer can include disclosed articles such as those discussed above and can include one or more oils, one or more polymer film formers and one or more humectants. In some embodiments, disclosed articles 103 can include at least a second layer, the optional second layer 105 an be adjacent to the first layer 104, as depicted in FIG. 1B. In some embodiments, the optional second layer can include one or more mucoadhesive polymers, for example. An article that includes an optional second layer that includes a mucoadhesive polymer could be utilized as the portion of the article that is put into contact with the roof of the user's mouth. This layer could then function to maintain the article in the mouth of the user while the first layer dissolves. Illustrative mucoadhesive polymers can include polyacrylates, hyaluronic acid, chitosan, cellulose derivatives, alginate, pectin, gelatin, or combinations thereof. In some embodiments, disclosed articles 106 could include an optional third layer 109. In such an embodiment, the first layer 107 could be positioned between the second layer 108 and the third layer 109, as seen in FIG. 1C. Additional materials that could be utilized in an optional second layer or even an optional third layer (in an embodiment that includes a second layer) could also include active agents that are desirably delivered to the mouth of a user. Illustrative such materials could include, for example, anti-microbial agents, Also disclosed herein are methods of using disclosed articles. Disclosed methods can include contacting an oral cavity or oral tissue with a disclosed article. The step of contacting the oral cavity or oral tissue can be accomplished by applying the article in any way, for example by simply placing the article in the mouth. Disclosed methods can be useful for preventing, inhibiting, disrupting, or any combination thereof the formation or maintenance of a biofilm in an area contacted with the article; for affecting hydration loss in an area contacted by the article; for affecting lubricity or lubriciousness of an area contacted by the article; for affecting or alleviating the effects of xerostomia, dry mouth, or both.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising" and the like. For example, a composition that "comprises" silver may be a composition that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects is present. For example, a "second" substrate is merely intended to differentiate from another substrate (such as a "first" substrate). Use of "first," "second," etc. in the description above and the claims that follow is also not necessarily intended to indicate that one comes earlier in time than the other.

Example articles and techniques according to the disclosure provide will be illustrated by the following non-limiting examples.

EXAMPLES

TABLE 1A

| Materials | | | |
|---|---|---|---|
| Chemical/Material Name | Abbreviation | CAS | Manufacturer |
| Water (Deionized) | Water | n/a | n/a |
| Pullulan | | | TCI America, Tokyo, Japan |
| Xanthan gum (KELTROL Advanced Performance) | Xanthan gum | 11138-66-2 | CP Kelco, Atlanta, GA |
| Carrageenan Iota | | | Sigma Aldrich, St. Louis, MO |
| HP guar (JAGUAR S) | | | Solvay Novecare, Belgium |
| Aqualon ™ EC-N50 PHARM ethy lcellulose | | | Ashland, Wilmington, DE |
| NEOBEE M5 Oil | | | Stepan, Maywood, NJ |
| Oleic acid | Oleic Acid | 112-80-1 | Spectrum Chem, New Brunswick, NJ |

TABLE 1A-continued

Materials

| Chemical/Material Name | Abbreviation | CAS | Manufacturer |
|---|---|---|---|
| Polyglyceryl-6-Disterate (POLYALDO 6-2-S) | POLYALDO 6-2-S | 34424-97-0 | Lonza, Basel, Switzerland |
| Polyglyceryl-10 Stearate (POLYALDO 10-1-S) | POLYALDO 10-1-S | 79777-30-3 | Lonza, Basel, Switzerland |
| Glycerol | | | VWR Scientific, Radnor, PA |
| Phosphate Buffer Saline | | | Gibco by Life Technologies |

TABLE 1B

Materials-Stock Solutions

| Solution Name | Quantity (g) | Wt.-% |
|---|---|---|
| Oil Phase 1 | | |
| Neobee M-5 | 36 | 84% |
| Oleic Acid | 4 | 9% |
| POLYALDO 6-2-S | 0.6 | 1% |
| POLYALDO 10-1-S | 2.4 | 6% |
| Oil Phase 2 | | |
| NEOBEE M-5 | 36 | 80% |
| Oleic Acid | 4 | 9% |
| POLYALDO 6-2-S | 0.6 | 1% |
| POLYALDO 10-1-S | 2.4 | 5% |

TABLE 1B-continued

Materials-Stock Solutions

| Solution Name | Quantity (g) | Wt.-% |
|---|---|---|
| Film Former Phase 1 | | |
| Xanthan gum solution (1 wt % in water) | 9.9 | 3% |
| Carrageenan (1 wt % in water) | 99.3 | 28% |
| Pullulan (25 wt % in water) | 190.8 | 55% |
| PBS Buffer | 48.8 | 14% |
| Film Former Phase 2 | | |
| Xanthan gum solution (1 wt % in water) | 12.8 | 3% |
| HP Guar solution (1 wt % in water) | 12.8 | 28% |
| Carrageenan (1 wt % in water) | 128.1 | 283% |
| Pullulan (25 wt % in water) | 246.3 | 544% |

Samples ID: F1-1 to F9-3

Dissolvable films were prepared by making an oil-in-water emulsion with an oil phase consisting of oil and emulsifiers and an aqueous phase consisting of film formers at varying concentrations in water and glycerol.

Aqueous (film former phase and glycerol) and oil phases were combined separately as described in Table 2 and heated to 80° C. The oil phase was poured into the aqueous phase and homogenized at medium speed for three minutes. The emulsion was rolled until it reached room temperature and then it was let sit until it was coated out to form a strip.

TABLE 2

| ID No | Amount of Stock Solution Added (g) | | | | | Percentage of Each Formulation Stock in Dry Film | | | | |
|---|---|---|---|---|---|---|---|---|---|---|
| | Oil Phase 1 | Phase Oil 2 | Film Phase 1 | Film Phase 2 | Glycerol | Oil Phase 1 | Phase 2 Oil | Film Former 1 | Film Former 2 | Glycerol |
| F1-1 | 4.57 | | 34.29 | | 1.14 | 44% | | 45% | | 11% |
| F1-2 | 4.28 | | 34.29 | | 1.43 | 41% | | 45% | | 14% |
| F1-3 | 3.81 | | 34.29 | | 1.90 | 37% | | 45% | | 18% |
| F2-1 | 3.21 | | 35.99 | | 0.80 | 36% | | 55% | | 9% |
| F2-2 | 3.01 | | 35.99 | | 1.00 | 34% | | 55% | | 11% |
| F2-3 | 2.67 | | 35.99 | | 1.34 | 30% | | 55% | | 15% |
| F3-1 | 2.19 | | 37.27 | | 0.55 | 28% | | 65% | | 7% |
| F3-2 | 2.05 | | 37.27 | | 0.68 | 26% | | 65% | | 9% |
| F3-3 | 1.82 | | 37.27 | | 0.91 | 23% | | 65% | | 12% |
| F4-1 | 3.21 | | | 35.99 | 0.80 | 36% | | | 55% | 9% |
| F4-2 | 3.01 | | | 35.99 | 1.00 | 34% | | | 55% | 11% |
| F4-3 | 2.67 | | | 35.99 | 1.34 | 30% | | | 55% | 15% |
| F5-1 | 2.19 | | | 37.27 | 0.55 | 28% | | | 65% | 7% |
| F5-2 | 2.05 | | | 37.27 | 0.68 | 26% | | | 65% | 9% |
| F5-3 | 1.82 | | | 37.27 | 0.91 | 23% | | | 65% | 12% |
| F6-1 | | 3.21 | | 35.99 | 0.80 | | 36% | | 55% | 9% |
| F6-2 | | 3.01 | | 35.99 | 1.00 | | 34% | | 55% | 11% |
| F6-3 | | 2.67 | | 35.99 | 1.34 | | 30% | | 55% | 15% |
| F7-1 | | 2.19 | | 37.27 | 0.55 | | 28% | | 65% | 7% |
| F7-2 | | 2.05 | | 37.27 | 0.68 | | 26% | | 65% | 9% |
| F7-3 | | 1.82 | | 37.27 | 0.91 | | 23% | | 65% | 12% |
| F8-1 | 3.21 | 35.99 | | | 0.80 | 36% | 55% | | | 9% |
| F8-2 | 3.01 | 35.99 | | | 1.00 | 34% | 55% | | | 11% |
| F8-3 | 2.67 | 35.99 | | | 1.34 | 30% | 55% | | | 15% |
| F9-1 | 2.19 | 37.27 | | | 0.55 | 28% | 65% | | | 7% |
| F9-2 | 2.05 | 37.27 | | | 0.68 | 26% | 65% | | | 9% |
| F9-3 | 1.82 | 37.27 | | | 0.91 | 23% | 65% | | | 12% |

Strip Preparation

A set amount of emulsion was coated onto a PET liner at 0.016 in thickness. The samples were then placed in an oven at 70° C. for 30 minutes. Each sample was evaluated for film stretchiness (stretch verses brittle feel), integrity, oil residue (high, medium, low), and feel (sticky versus not sticky, oily versus not oily).

TABLE 3A

|  | Comparative Examples CE1-CE4; Examples EX1-EX2 | | | | | |
|---|---|---|---|---|---|---|
| EXAMPLE: | CE1 | CE2 | CE3 | EX1 | EX2 | CE4 |
| Oil Phase | F1-1 | F1-2 | F1-3 | F2-1 | F2-2 | F2-3 |
| NEOBEE M-5 | 36.2% | 34.0% | 30.2% | 29.5% | 27.7% | 24.6% |
| Oleic Acid | 4.03% | 3.78% | 3.36% | 3.28% | 3.08% | 2.74% |
| POLYALDO 6-2-S | 0.60% | 0.57% | 0.50% | 0.49% | 0.46% | 0.41% |
| POLYALDO 10-1-S | 2.42% | 2.27% | 2.01% | 1.97% | 1.85% | 1.64% |
| Total % Plant-based oils: | 40.3% | 37.8% | 33.6% | 32.8% | 30.8% | 27.4% |
| Total % Oil Phase: | 43.3% | 40.6% | 36.1% | 35.3% | 33.1% | 29.4% |
| Water Phase | | | | | | |
| Ethyl Cellulose* | 0% | 0% | 0% | 0% | 0% | 0% |
| Xanthan Gum* | 0.09% | 0.09% | 0.09% | 0.11% | 0.11% | 0.11% |
| HP Guar* | 0% | 0% | 0% | 0% | 0% | 0% |
| Carrageenan* | 0.92% | 0.92% | 0.92% | 1.13% | 1.13% | 1.13% |
| Pullulan* | 44.4% | 44.4% | 44.4% | 54.1% | 54.1% | 54.1% |
| Phosphate Salts | 0.08% | 0.08% | 0.08% | 0.09% | 0.09% | 0.09% |
| NaCl | 0.36% | 0.36% | 0.36% | 0.44% | 0.44% | 0.44% |
| KCl | 0.0009% | 0.0009% | 0.0009% | 0.0011% | 0.0011% | 0.0011% |
| Glycerol | 10.8% | 13.5% | 18.0% | 8.8% | 11.0% | 14.7% |
| *Total % film-formers: | 45.5% | 45.5% | 45.5% | 55.4% | 55.4% | 55.4% |
| Total % Water Phase: | 56.7% | 59.4% | 63.9% | 64.7% | 66.9% | 70.6% |
| % Total: | 100% | 100% | 100% | 100% | 100% | 100% |
| Acceptable (Integrity, No oily feel, No oil visible) | No | No | No | Yes | Yes | Yes |

TABLE 3B

|  | Examples EX3-EX5; Comparative Examples CE5-CE7 | | | | | |
|---|---|---|---|---|---|---|
| EXAMPLE: | EX3 | EX4 | EX5 | CE5 | CE6 | CE7 |
| Oil Phase | F3-1 | F3-2 | F3-3 | F4-1 | F4-2 | F4-3 |
| NEOBEE M-5 | 22.9% | 21.5% | 19.1% | 30.0% | 28.1% | 25.0% |
| Oleic Acid | 2.54% | 2.39% | 2.12% | 3.33% | 3.12% | 2.78% |
| POLYALDO 6-2-S | 0.38% | 0.36% | 0.32% | 0.50% | 0.47% | 0.42% |
| POLYALDO 10-1-S | 1.53% | 1.43% | 1.27% | 2.00% | 1.87% | 1.67% |
| Total % Plant-based oils: | 25.4% | 23.9% | 21.2% | 33.3% | 31.2% | 27.8% |
| Total % Oil Phase: | 27.4% | 25.6% | 22.8% | 35.8% | 33.6% | 29.8% |
| Water Phase | | | | | | |
| Ethyl Cellulose* | 0% | 0% | 0% | 0% | 0% | 0% |
| Xanthan Gum* | 0.13% | 0.13% | 0.13% | 0.11% | 0.11% | 0.11% |
| HP Guar* | 0% | 0% | 0% | 0.11% | 0.11% | 0.11% |
| Carrageenan | 1.33% | 1.33% | 1.33% | 1.11% | 1.11% | 1.11% |
| Pullulan* | 63.7% | 63.7% | 63.7% | 53.4% | 53.4% | 53.4% |
| Phosphate Salts | 0.11% | 0.11% | 0.11% | 0.09% | 0.09% | 0.09% |

TABLE 3B-continued

| | | Examples EX3-EX5; Comparative Examples CE5-CE7 | | | | |
|---|---|---|---|---|---|---|
| EXAMPLE: | EX3 | EX4 | EX5 | CE5 | CE6 | CE7 |
| NaCl | 0.52% | 0.52% | 0.52% | 0.43% | 0.43% | 0.43% |
| KCl | 0.0013% | 0.0013% | 0.0013% | 0.0011% | 0.0011% | 0.0011% |
| Glycerol | 6.8% | 8.5% | 11.4% | 9.0% | 11.2% | 14.9% |
| *Total % film-formers: | 65.2% | 65.2% | 65.2% | 54.7% | 54.7% | 54.7% |
| Total % Water Phase: | 72.6% | 74.4% | 77.2% | 64.2% | 66.4% | 70.2% |
| % Total: | 100% | 100% | 100% | 100% | 100% | 100% |
| Acceptable (Integrity, No oily feel, No oil visible) | Yes | Yes | Yes | No | No | No |

TABLE 3C

| | | Comparative Examples CE8-CE13 | | | | |
|---|---|---|---|---|---|---|
| EXAMPLE: | CE8 | CE9 | CE10 | CE11 | CE12 | CE13 |
| Oil Phase | F5-1 | F5-2 | F5-3 | F6-1 | F6-2 | F6-3 |
| NEOBEE M-5 | 23.3% | 21.8% | 19.4% | 28.5% | 26.7% | 23.7% |
| Oleic Acid | 2.59% | 2.43% | 2.16% | 3.16% | 2.97% | 2.64% |
| POLYALDO 6-2-S | 0.39% | 0.36% | 0.32% | 0.47% | 0.45% | 0.40% |
| POLYALDO 10-1-S | 1.55% | 1.46% | 1.29% | 1.90% | 1.78% | 1.58% |
| Total % Plant-based oils: | 25.9% | 24.3% | 21.6% | 31.6% | 29.7% | 26.4% |
| Total % Oil Phase: | 27.8% | 26.1% | 23.2% | 34.0% | 31.9% | 28.4% |
| Water Phase | | | | | | |
| Ethyl Cellulose* | 0% | 0% | 0% | 1.79% | 1.68% | 1.49% |
| Xanthan Gum | 0.13% | 0.13% | 0.13% | 0.11% | 0.11% | 0.11% |
| HP Guar* | 0.13% | 0.13% | 0.13% | 0.11% | 0.11% | 0.11% |
| Carrageenan | 1.31% | 1.31% | 1.31% | 1.11% | 1.11% | 1.11% |
| Pullulan* | 63.0% | 63.0% | 63.0% | 53.4% | 53.4% | 53.4% |
| Phosphate Salts | 0.11% | 0.11% | 0.11% | 0.09% | 0.09% | 0.09% |
| NaCl | 0.51% | 0.51% | 0.51% | 0.43% | 0.43% | 0.43% |
| KCl | 0.0013% | 0.0013% | 0.0013% | 0.0011% | 0.0011% | 0.0011% |
| Glycerol | 7.0% | 8.7% | 11.6% | 9.0% | 11.2% | 14.9% |
| *Total % film-formers: | 64.6% | 64.6% | 64.6% | 56.5% | 56.4% | 56.2% |
| Total % Water Phase: | 72.2% | 73.9% | 76.8% | 66.0% | 68.1% | 71.6% |
| % Total: | 100% | 100% | 100% | 100% | 100% | 100% |
| Acceptable (Integrity, No oily feel, No oil visible) | No | No | No | No | No | No |

TABLE 3D

| | | Examples EX6-EX8; Comparative Examples CE14-CE16 | | | | |
|---|---|---|---|---|---|---|
| EXAMPLE: | EX6 | EX7 | EX8 | CE14 | CE15 | CE16 |
| Oil Phase | F7-1 | F7-2 | F7-3 | F8-1 | F8-2 | F8-3 |
| NEOBEE M-5 | 22.1% | 20.7% | 18.4% | 28.1% | 26.3% | 23.4% |
| Oleic Acid | 2.46% | 2.31% | 2.05% | 3.12% | 2.92% | 2.60% |
| POLYALDO 6-2-S | 0.37% | 0.35% | 0.31% | 0.47% | 0.44% | 0.39% |

TABLE 3D-continued

| Examples EX6-EX8; Comparative Examples CE14-CE16 | | | | | | |
|---|---|---|---|---|---|---|
| EXAMPLE: | EX6 | EX7 | EX8 | CE14 | CE15 | CE16 |
| POLYALDO 10-1-S | 1.48% | 1.38% | 1.23% | 1.87% | 1.75% | 1.56% |
| Total % Plant-based oils: | 24.6% | 23.1% | 20.5% | 31.2% | 29.2% | 26.0% |
| Total % Oil Phase: | 26.4% | 24.8% | 22.0% | 33.5% | 31.4% | 27.9% |
| Water Phase | | | | | | |
| Ethyl Cellulose* | 1.39% | 1.30% | 1.16% | 1.76% | 1.65% | 1.47% |
| Xanthan Gum* | 0.13% | 0.13% | 0.13% | 0.11% | 0.11% | 0.11% |
| HP Guar* | 0.13% | 0.13% | 0.13% | 0.00% | 0.00% | 0.00% |
| Carrageenan* | 1.31% | 1.31% | 1.31% | 1.13% | 1.13% | 1.13% |
| Pullulan* | 63.0% | 63.0% | 63.0% | 54.1% | 54.1% | 54.1% |
| Phosphate Salts | 0.11% | 0.11% | 0.11% | 0.09% | 0.09% | 0.09% |
| NaCl | 0.51% | 0.51% | 0.51% | 0.44% | 0.44% | 0.44% |
| KCl | 0.0013% | 0.0013% | 0.0013% | 0.0011% | 0.0011% | 0.0011% |
| Glycerol | 7.0% | 8.7% | 11.6% | 8.8% | 11.0% | 14.7% |
| *Total % film-formers: | 66.0% | 65.9% | 65.8% | 57.1% | 57.0% | 56.8% |
| Total % Water Phase: | 73.6% | 75.2% | 78.0% | 66.5% | 68.6% | 72.1% |
| % Total: | 100% | 100% | 100% | 100% | 100% | 100% |
| Acceptable (Integrity, No oily feel, No oil visible) | Yes | Yes | Yes | No | No | No |

TABLE 3E

| Comparative Example CE17; Examples EX9-EX10 | | | |
|---|---|---|---|
| EXAMPLE: | CE17 | EX9 | EX10 |
| Oil Phase | F9-1 | F9-2 | F9-3 |
| NEOBEE M-5 | 21.8% | 20.4% | 18.1% |
| Oleic Acid | 2.42% | 2.27% | 2.01% |
| POLYALDO 6-2-S | 0.36% | 0.34% | 0.30% |
| POLYALDO 10-1-S | 1.45% | 1.36% | 1.21% |
| Total % Plant-based oils: | 24.2% | 22.7% | 20.1% |
| Total % Oil Phase: | 26.0% | 24.4% | 21.7% |
| Water Phase | | | |
| Ethyl Cellulose* | 1.37% | 1.28% | 1.14% |
| Xanthan Gum* | 0.13% | 0.13% | 0.13% |
| HP Guar* | 0.00% | 0.00% | 0.00% |
| Carrageenan* | 1.33% | 1.33% | 1.33% |
| Pullulan* | 63.7% | 63.7% | 63.7% |
| Phosphate Salts | 0.11% | 0.11% | 0.11% |
| NaCl | 0.52% | 0.52% | 0.52% |
| KCl | 0.0013% | 0.0013% | 0.0013% |
| Glycerol | 6.8% | 8.5% | 11.4% |
| *Total % film-formers: | 66.6% | 66.5% | 66.3% |
| Total % Water Phase: | 74.0% | 75.6% | 78.3% |
| % Total: | 100% | 100% | 100% |
| Acceptable (Integrity, No oily feel, No oil visible) | No | Yes | Yes |

TABLE 4

| EX. | ID# | Gly-cerol | Integrity | Not Sticky? | No Oil Visible | No Oil Feel to the touch | Overall Accept-able? |
|---|---|---|---|---|---|---|---|
| CE1 | F1-1 | 10.8% | good | − | − − | − − | No |
| CE2 | F1-2 | 13.5% | stretchy, pulls apart | − | − − | − − | No |
| CE3 | F1-3 | 18.0% | stretchy, pulls apart | + | − − | − − | No |
| EX1 | F2-1 | 8.8% | good | + | − | + | Yes |
| EX2 | F2-2 | 11.0% | good | + | − | + | Yes |
| CE4 | F2-3 | 14.7% | strong, yet breaks | + | − − | − − | No |
| EX3 | F3-1 | 6.8% | brittle, tearable | + | + | + | Yes |
| EX4 | F3-2 | 8.5% | brittle, tearable | + | + | + | Yes |
| EX5 | F3-3 | 11.4% | brittle, tearable | + | − | + | Yes |
| CE5 | F4-1 | 9.0% | brittle, cracking | + | − − | + | No |
| CE6 | F4-2 | 11.2% | brittle, cracking | − | − − | + | No |
| CE7 | F4-3 | 14.9% | brittle | + | − − | − − | No |
| CE8 | F5-1 | 7.0% | brittle, tearable | + | − − | − − | No |
| CE9 | F5-2 | 8.7% | brittle, tearable | + | − − | − | No |
| CE10 | F5-3 | 11.6% | brittle, tearable | + | − − | − | No |
| CE11 | F6-1 | 9.0% | brittle, cracking | + | − − | − − | No |
| CE12 | F6-2 | 11.2% | brittle | + | − | − − | No |
| CE13 | F6-3 | 14.9% | stretchy | − | − − | − − | No |
| EX6 | F7-1 | 7.0% | brittle, tearable | + | + | + | Yes |
| EX7 | F7-2 | 8.7% | brittle, tearable | + | + | + | Yes |
| EX8 | F7-3 | 11.6% | brittle, tearable | + | + | + | Yes |
| CE14 | F8-1 | 8.8% | brittle | + | − − | − − | No |
| CE15 | F8-2 | 11.0% | brittle | + | − − | − − | No |
| CE16 | F8-3 | 14.7% | dead stretch | + | − − | − − | No |
| CE17 | F9-1 | 6.8% | brittle, tearable | + | − − | − − | No |
| EX9 | F9-2 | 8.5% | good | + | + | − | Yes |
| EX10 | F9-3 | 11.4% | good | + | + | − | Yes |

"+" = good/true
"−" = poor/not true
"− −" = very poor/not true.

Strip properties were observed by visual observation of oil left on a polyethylene (PET) liner. Also, films were handled to determine the feel and integrity of the film. These observations are recorded in Table 4. Desirable films are those that have low oil residue, low oil feel, are not sticky, and have good integrity.

Dissolution Study

One drop of blue food coloring (F4-2, F5-2, F6-2, F7-2) or Nile red dye (F1-2, F2-2, F8-2, and F-9-2) in oil was added to the emulsion formulation before coating onto the PET liner. Samples were then coated and dried as previously described. Sample punches (1.3 cm diameter circles) were then cut from the blue strip samples for the dissolution studies. Samples were placed on the side of a test tube and put into 37° C. DI water. The test tube was suspended above a stir bar such that the solution was being stirred while the sample was suspended. The visual dissolution was monitored over 10 minutes.

LISTERINE POCKETPAKS® Oral Care Breath Strips were used as a control.

Dissolution studies were performed on select strips to see the effects of different thickeners in the film forming phase and the effect of hydroxyethyl cellulose in the oil phase. Table 5 contains the observed dissolution data at 5 and 10 minutes. All the films had similar film former composition but there is a difference in dissolution rate of the films tested. Table 5 summarizes the results of the dissolution study.

TABLE 5

| Example Formulation | Dissolution 5 minutes | Dissolution 10 minutes | Other observations |
|---|---|---|---|
| LISTERINE Strip | >50% | >90% | — |
| CE2 (F1-2, Nile red dye) | >50% | >75% | Coming off in chunks |
| EX2 (F2-2, Nile red dye) | <50% | >75% | Lubricious/oil feel at 10 min. |
| CE6 (F4-2, Blue food coloring) | <50% | >50% | Lubricious/oil feel at 10 min. |
| CE9 (F5-2, Blue food coloring) | >50% | >90% | No oily feel at 10 min. |
| CE12 (F6-2, Blue food coloring) | >50% | >90% | Little/no oily feel at 10 min. |
| EX7 (F7-2, Blue food coloring) | >50% | >90% | Little oily feel at 10 min. |
| CE15 (F8-2, Nile red dye) | <50% | >50% | Lubricious/oil feel at 10 min. |
| EX9 (F9-2, Nile red dye) | >50% | >90% | Lubricious/oil feel at 10 min. |

Illustrative Embodiments:

An article including from 20 wt-% to 45 wt-% of one or more plant based oils based on the total weight of the article; from 50 wt-% to 70 wt-% of one or more polymer film formers based on the total weight of the article; and from 5 wt-% to 15 wt-% of one or more humectants based on the total weight of the article.

Articles according to any of the above embodiments, wherein the one or more plant based oils are selected from: sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, watermelon seed oil, lemon oil, orange oil, thistle oil, tomato seed oil, almond oil, *perilla* oil, canola oil, pistachio oil, hazelnut oil, *camellia* seed oil, shea nut oil, macadamia nut oil, apricot kernel oil, oleic acid, ozonated oils and avocado oil.

Articles according to any of the above embodiments, wherein the one or more plant based oils are present in an amount from 20 wt-% to 35 wt-% based on the total weight of the article.

Articles according to any of the above embodiments, wherein the one or more plant based oils are present in an amount from 23 wt-% to 28 wt-% based on the total weight of the article.

Articles according to any of the above embodiments, wherein the one or more plant based oils are present in an amount from 30 wt-% to 45 wt-% based on the total weight of the article.

Articles according to any of the above embodiments, wherein the one or more polymer film formers are selected from: pullulan, hydroxypropylmethyl cellulose, hydroxyethyl cellulose, ethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein, xanthan gum, locust bean gum, carrageenan, and combinations thereof.

Articles according to any of the above embodiments, wherein the one or more polymer film formers comprise a combination of pullulan, xanthan gum, HP guar, ethyl cellulose, and carrageenan.

Articles according to any of the above embodiments, wherein the one or more polymer film formers are present in an amount from 52 wt-% to 67 wt-% based on the total weight of the article.

Articles according to any of the above embodiments, wherein the one or more polymer film formers are present in an amount from 55 wt-% to 65 wt-% based on the total weight of the article.

Articles according to any of the above embodiments, wherein the one or more humectants are selected from glycerol, sorbitol, xylitol, maltitol, propylene glycol, hexylene glycol, butylene glycol, erythritol, isomalt, and combinations thereof.

Articles according to any of the above embodiments, wherein the one or more humectants are selected from glycerol, xylitol, erythritol, and combinations thereof.

Articles according to any of the above embodiments, wherein the one or more humectants are present in an amount from 7 wt-% to 14 wt-% based on the total weight of the article.

Articles according to any of the above embodiments, wherein the one or more humectants are present in an amount from 7 wt-% to 12 wt-% based on the total weight of the article.

Articles according to any of the above embodiments further comprising sweeteners, mineral salts, buffering components, flavorants, preservative agents, or combinations thereof.

Articles according to any of the above embodiments further comprising aloe vera, folic acid, hyaluronic acid, ceramides, arginine, betaines or oxygenated glycerol triesters, vitamin E, vitamin B12, EDTA, cetyl pyridinium chloride, chlorhexidine, other antiseptics, or combinations thereof.

Articles according to any of the above embodiments, wherein the article comprises from 1 wt-% to 20 wt-% sweeteners based on the total weight of the article.

Articles according to any of the above embodiments, in the form of a solid strip.

Articles according to any of the above embodiments, in the form of a roll of a solid strip.

Articles according to any of the above embodiments, wherein the article can prevent, inhibit, disrupt, or any combination thereof the formation or maintenance of a biofilm in an area contacted with the article.

Articles according to any of the above embodiments, wherein the article can affect hydration loss in an area contacted by the article.

Articles according to any of the above embodiments, wherein the article can affect lubricity or lubriciousness of an area contacted by the article.

Methods of preventing, inhibiting, disrupting, or any combination thereof the formation or maintenance of a biofilm in an oral tissue, the method comprising: contacting an oral tissue with articles according to any of the above embodiments.

Methods of affecting hydration loss in an oral tissue, the method comprising: contacting an oral tissue with articles according to any of the above embodiments.

Methods of affecting lubricity or lubriciousness in an oral tissue, the method comprising:
contacting an oral tissue with articles according to any of the above embodiments.

Methods of affecting the effects of xerostomia, dry mouth, or both, the method comprising:
contacting an oral tissue with articles according to any of the above embodiments.

Articles comprising: a first layer comprising from 20 wt-% to 45 wt-% of one or more plant based oils based on the total weight of the article; from 50 wt-% to 70 wt-% of one or more polymer film formers based on the total weight of the article; and from 5 wt-% to 15 wt-% of one or more humectants based on the total weight of the article; and a second layer adjacent to the first layer, the second layer comprising a mucoadhesive polymer.

Articles according to any of the above embodiments, wherein the mucoadhesive polymer is selected from polyacrylates, hyaluronic acid, chitosan, cellulose derivatives, alginate, pectin, gelatin, or combinations thereof.

Articles according to any of the above embodiments further comprising a third layer adjacent the first layer and wherein the first layer is between the second layer and the third layer.

Articles according to any of the above embodiments, wherein the third layer comprises an antimicrobial agent, a numbing agent (e.g., benzocaine), or combinations thereof.

Thus embodiments of oral compositions and methods of use are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:
1. An article comprising:
one or more plant-based oil present in amount from 20 wt-% to 45 wt-%,
the plant-based oil selected from medium-chain triglycerides, sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, watermelon seed oil, thistle oil, tomato seed oil, almond oil, perilla oil, canola oil, pistachio oil, hazelnut oil, camellia seed oil, shea nut oil, macadamia nut oil, apricot kernel oil, and avocado oil;
pullulan as polymer film former, pullulan present in amount from 50 wt-% to 70 wt-%;
optionally one or more additional polymer film former,

wherein pullulan and the one or more additional polymer film formers are present in a total amount from 50 wt-% to 70 wt-%; and
one or more humectants present in an amount from 5 wt-% to 15 wt-%; and
an emulsifier,
wherein the article is an emulsion and in the form of a solid strip, roll, or tape, and
wherein each wt-% is with respect to the weight of the article.

2. The article according to claim 1, wherein the one or more plant-based oil is caprylic/capric triglycerides.

3. The article according to claim 1, wherein the one or more plant-based oil is present in an amount from 23 wt-% to 28 wt-% with respect to the weight of the article.

4. The article according to claim 1, wherein the one or more additional polymer film former is selected from: hydroxypropylmethyl cellulose, hydroxyethyl cellulose, ethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein, xanthan gum, locust bean gum, carrageenan, and a combination thereof.

5. The article according to claim 1, the one or more additional polymer film former selected from xanthan gum, HP guar, ethyl cellulose, carrageenan, and a combination thereof.

6. The article according to claim 1, wherein the one or more humectant is selected from glycerol, sorbitol, xylitol, maltitol, propylene glycol, hexylene glycol, butylene glycol, erythritol, isomalt, and a combination thereof.

7. A method of one or more of preventing, inhibiting, and disrupting the formation or maintenance of a biofilm in an oral tissue, the method comprising:
contacting an oral tissue with an article according to claim 1.

8. A method of reducing hydration loss in an oral tissue, the method comprising:
contacting an oral tissue with an article according to claim 1.

9. A method of increasing lubricity or lubriciousness in an oral tissue, the method comprising:
contacting an oral tissue with an article according to claim 1.

10. A method of decreasing the effects of xerostomia, dry mouth, or both, the method comprising:
contacting an oral tissue with an article according to claim 1.

11. An article comprising:
a first layer comprising:
one or more plant-based oil present in amount from 20 wt-% to 45 wt-%,
the plant-based oil selected from medium-chain triglycerides, sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, watermelon seed oil, thistle oil, tomato seed oil, almond oil, perilla oil, canola oil, pistachio oil, hazelnut oil, *camellia* seed oil, shea nut oil, macadamia nut oil, apricot kernel oil, and avocado oil, pullulan as polymer film former, pullulan present in an amount from 50 wt-% to 70 wt-%, optionally one or more additional polymer film former, wherein pullulan and the one or more additional polymer film formers are present in a total amount from 50 wt-% to 70 wt-%, one or more humectant present in an amount from 5 wt-% to 15 wt-%, and an emulsifier, and a second layer adjacent to the first layer, the second layer comprising a mucoadhesive polymer, wherein the first layer is an emulsion, wherein the article is in the form of a solid strip, roll, or tape, and wherein each wt-% is with respect to the weight of the article.

12. The article according to claim 11, wherein the mucoadhesive polymer is selected from polyacrylates, hyaluronic acid, chitosan, cellulose derivatives, alginate, pectin, gelatin, and a combination thereof.

13. The article according to claim 11, further comprising a third layer, the third layer comprising one or more of an antimicrobial agent and a numbing agent, wherein the first layer is between the second layer and the third layer.

14. The article of claim 1, wherein the emulsifier is a polyglyceryl ester.

15. The article of claim 1, comprising caprylic/capric triglycerides, and glycerol.

16. The article of claim 1, wherein the one or more plant-based oil is present in an amount of 20 wt % to 36 wt %, and pullulan is present in an amount of 55 wt % to 70 wt %, wherein the article excludes ethyl cellulose and HP Guar.

17. The article of claim 1, wherein the one or more plant-based oil present in an amount of 20 wt % to 28 wt %, and the pullulan is present in an amount of 65 wt % to 70 wt %, the article further comprising ethyl cellulose as an additional polymer film former.

18. A method of one or more of preventing, inhibiting, and disrupting the formation or maintenance of a biofilm in an oral tissue, the method comprising:

contacting an oral tissue with an article according to claim 11.

19. A method of one or more of:

reducing hydration loss in an oral tissue, and increasing lubricity or lubriciousness in an oral tissue, the method comprising:

contacting an oral tissue with an article according to claim 11.

20. A method of decreasing the effects of xerostomia, dry mouth, or both, the method comprising: contacting an oral tissue with an article according to claim 11.

* * * * *